United States Patent [19]

Wilson et al.

[11] Patent Number: 5,554,164
[45] Date of Patent: Sep. 10, 1996

[54] CURVED KNIFE FOR LINEAR STAPLERS

[75] Inventors: Donald F. Wilson, Shelton; Randolph F. Lehn, Stratford; Frank Dworak, Rocky Hill; Roy D. Gravener, Fairfield; Joseph E. Kus, Norwalk; Ralph A. Stearns, Bozrah, all of Conn.

[73] Assignee: United States Surgical Corporation, Norwalk, Conn.

[21] Appl. No.: 415,026

[22] Filed: Mar. 30, 1995

Related U.S. Application Data

[63] Continuation of Ser. No. 133,490, Oct. 7, 1993, abandoned.
[51] Int. Cl.⁶ .......................... A61B 17/62; A61B 17/08; B31B 1/00
[52] U.S. Cl. ........................ 606/167; 606/220; 227/19
[58] Field of Search .................. 606/79, 80, 82, 606/83, 85, 167, 175, 176, 179, 180, 183, 220, 139, 142, 143

[56] References Cited

U.S. PATENT DOCUMENTS

| | | | |
|---|---|---|---|
| 864,812 | 9/1907 | Thuillier | 606/167 |
| 2,455,655 | 12/1948 | Carroll | 606/82 |
| 3,079,606 | 1/1963 | Bobrov et al. | |
| 3,490,675 | 1/1970 | Green et al. | |
| 4,349,028 | 9/1982 | Green | |
| 4,409,973 | 10/1983 | Neufeld | 606/82 |
| 4,508,253 | 4/1985 | Green | |
| 4,520,817 | 6/1985 | Green | |
| 4,633,874 | 1/1987 | Chow et al. | |
| 4,784,137 | 11/1988 | Kulic et al. | |
| 4,944,744 | 7/1990 | Ray | 606/79 |
| 4,955,888 | 9/1990 | Slocum | 606/82 |
| 5,040,715 | 8/1991 | Green et al. | |
| 5,104,394 | 4/1992 | Knoepfler | 606/143 |
| 5,133,719 | 7/1992 | Winston | 606/79 |
| 5,156,315 | 10/1992 | Green et al. | |
| 5,156,614 | 10/1992 | Green et al. | |
| 5,217,476 | 6/1993 | Wishinsky | |
| 5,217,477 | 6/1993 | Lager | |

FOREIGN PATENT DOCUMENTS

| | | | |
|---|---|---|---|
| 488768 | 6/1992 | European Pat. Off. | |
| 1115740 | 9/1984 | U.S.S.R. | 606/79 |
| 1210524 | 10/1970 | United Kingdom | |

*Primary Examiner*—Michael A. Brown

[57] ABSTRACT

A knife for use with surgical fastening instrument for applying fasteners to tissue, the knife including a nonlinear cutting edge having a first portion, a second portion, and an intermediate between said first and said second portion, said first portion being positioned at least as distal as said intermediate portion. The cutting edge is configured to completely sever selected tissue while minimizing the potential for "wisping" of uncut or partially cut tissue away from the cutting edge.

18 Claims, 7 Drawing Sheets

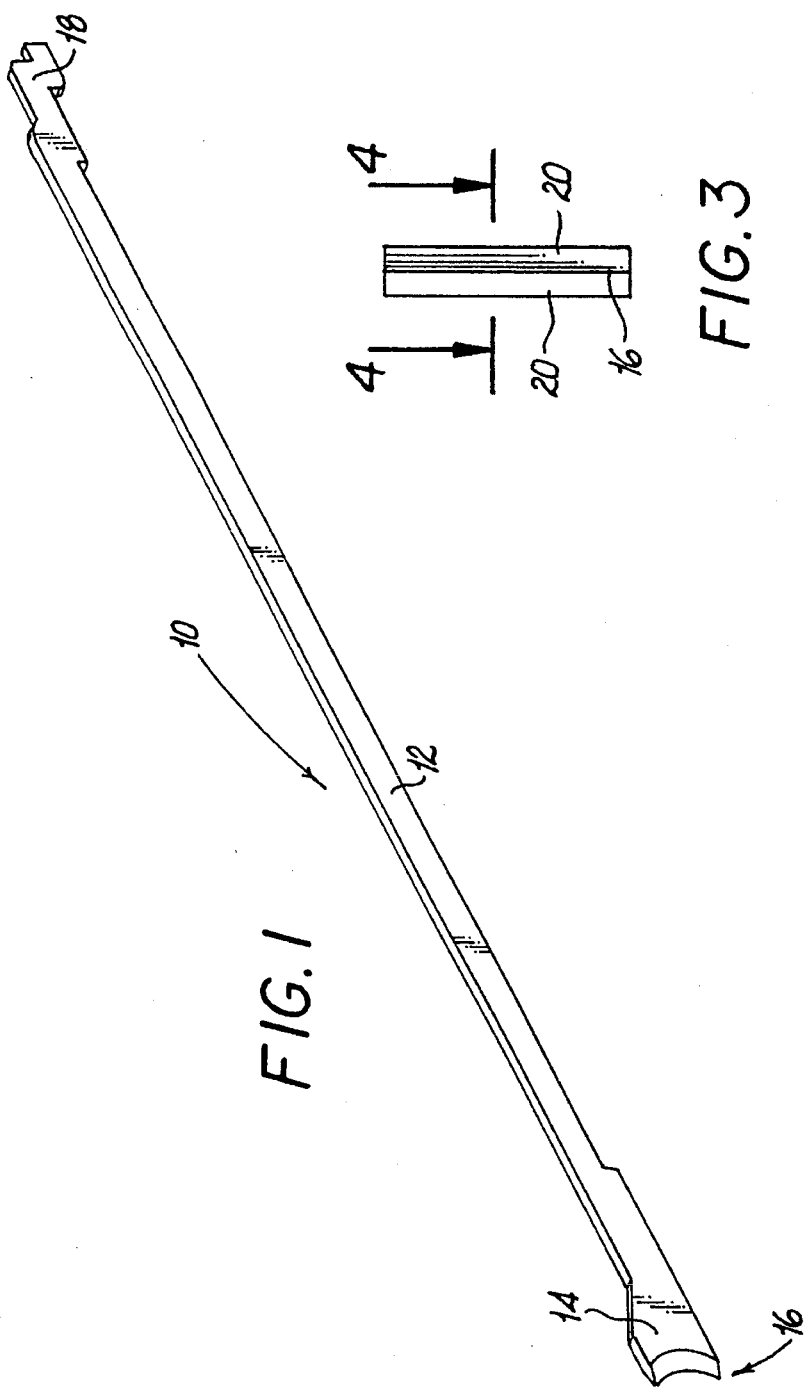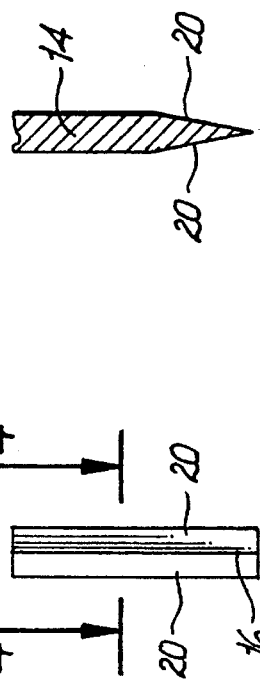

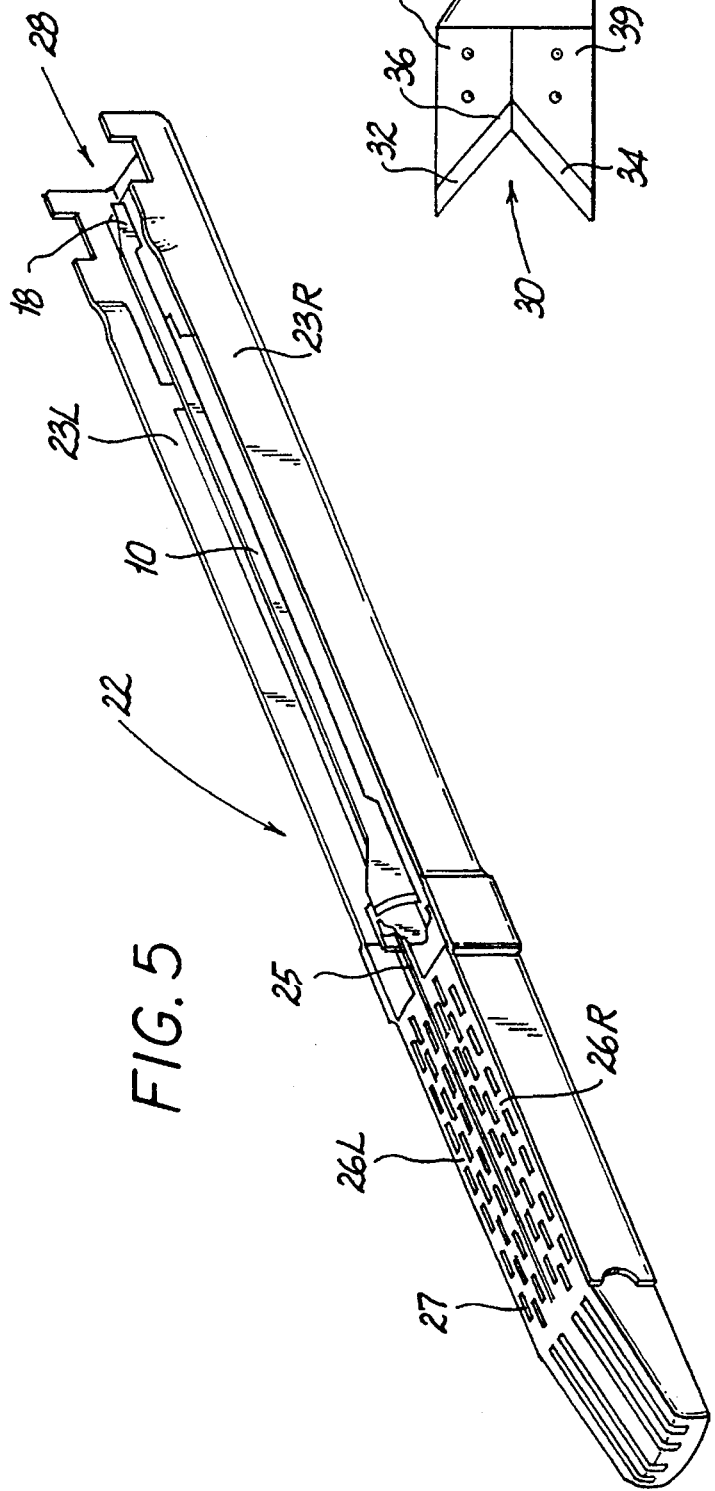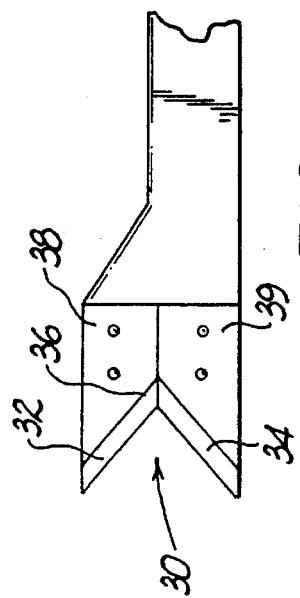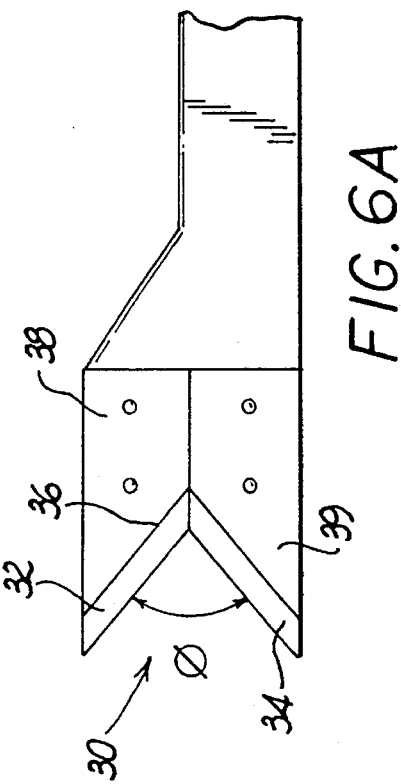

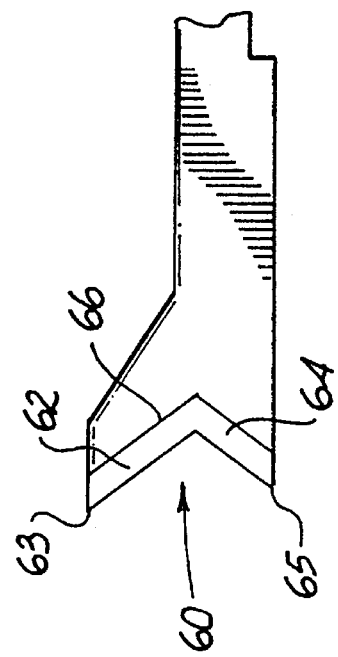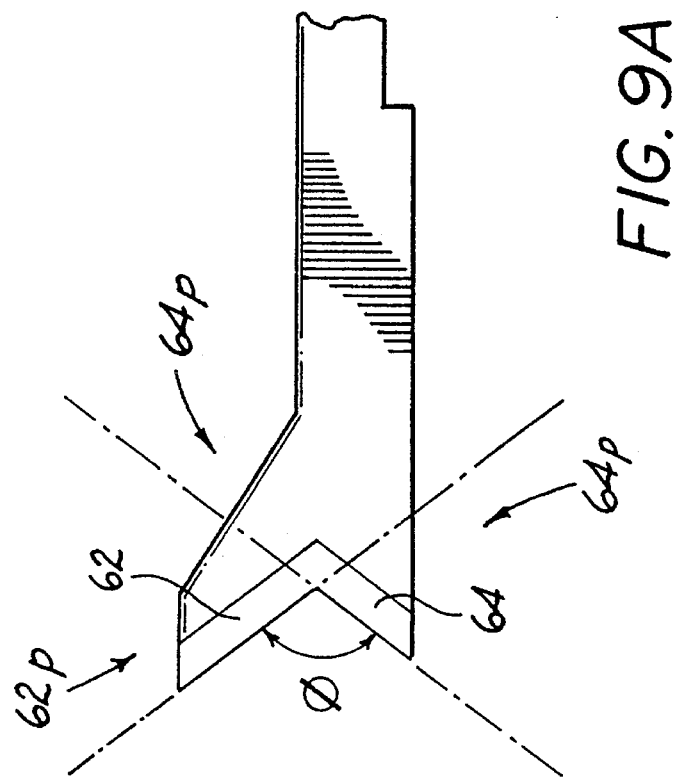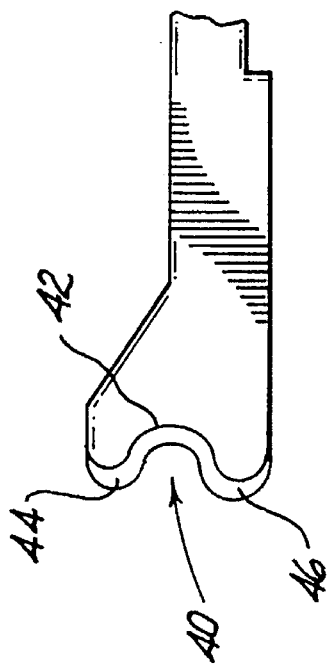

CURVED KNIFE FOR LINEAR STAPLERS

This is a continuation of application Ser. No. 08/133,490, filed on Oct. 7, 1993, now abandoned.

BACKGROUND OF THE INVENTION

1. Field of the Invention

This invention relates to an apparatus for applying surgical fasteners to body tissue and for severing body tissue with a knife, and more particularly to an improved knife having a non-linear cutting edge for severing tissue when the cutting edge engages body tissue.

2. Description of the Related Art

In recent years, endoscopic, laparoscopic, and arthroscopic surgical procedures have become increasingly common. Endoscopic, laparoscopic, and arthroscopic procedures require the surgeon to cut organs, tissues and vessels far removed from an;entry point into the body. In such procedures, the time and space to perform surgery is critical. Performing the procedure with the least number of devices possible reduces the risk of surgeon error, infection, and other potential complications associated with subsequent reintroduction of instrumentation into the body. As a result, multipurpose instruments capable of severing and adjoining tissue were developed to perform both functions during a single placement within a body.

In these surgical operations it is often necessary to adjoin two hollow body organs along side each other, with their longitudinal axes positioned generally parallel to each other, and to effect a longitudinal cut through the contacting circumferential walls of the two organs in order to open them to each other. After joining the two organs, they essentially constitute a single hollow chamber along the length of the cut. Correspondingly, the circumferential portions of the two adjoining organs on each lateral side of the cut must be sutured by at least one line of "stitches" in order to maintain the integrity of the union.

Instruments capable of performing both the severing and adjoining of tissue are known in the art, and are described in U.S. Pat. Nos. 3,079,606, 3,490,675 and 3,499,591. Such multipurpose instruments are generally referred to as linear cutting staplers and typically include two elongated fingers which are respectively insertable into the tissue or into each organ from an open end thereof such that the two fingers have the adjoining walls of adjacent organs therebetween.

One of the fingers includes a cartridge carrying a plurality of fasteners, typically staples, arranged in at least two lateral rows while the other finger includes an anvil for curling the staple's legs into a "B-shape" upon being driven against the anvil. The stapling operation is effected by a pusher device which travels longitudinally along the cartridge carrying finger extending into one organ. The pusher mechanism acts simultaneously upon the staples at corresponding longitudinal positions in each lateral row, but successively acts upon the staples along the rows. For example, if two lateral rows of staples are provided, each row comprising twenty staples, the pusher means acts upon two staples at a time, one in each row, and successively acts upon each succeeding pair of staples.

Immediately behind the pusher means and laterally positioned between the staple rows is a knife which severs the tissue of the two organs to thereby longitudinally open the two organs to each other between the rows of staples.

up to the present, these devices were limited to severing tissue by means of a knife having a linear cutting blade. For example, the apparatus disclosed in U.S. Pat. No. 5,040,715, hereby incorporated by reference, includes a knife having a linear cutting edge surface. Further examples of such instruments are disclosed in commonly assigned U.S. Pat. Nos. 5,156,614, 5,156,315, 5,014,899, 4,520,817, 4,508,253, and 4,349,028. The disclosures of these six last mentioned patents are additionally incorporated herein by reference.

Occasionally, when tough or resilient tissue, such as ligament and/or tendon, comes into contact with known linear cutting edges, the tissue may only be partially severed. Specifically, as the linear cutting edge encounters the tough tissue, the application of cutting force against the tissue may produce an upward or lifting force on the tissue. As the cutting edge severs the tissue, the geometry of the cutting edge may permit the upper portion of the tissue to "ride up" the cutting edge and into contact with the upper finger of the apparatus. The upper finger of the apparatus may flex a sufficient amount under the force of the knife severing tissue to permit a thin layer of uncut tissue to slide therebetween. This uncut layer of tissue is referred to as a wisp. The knife, synchronized with the stapling operation so as to act only in conjunction therewith, cannot be reapplied to the wisp independent of an additional stapling operation. The remaining wisp necessitates a subsequent introduction of instrumentation to completely sever the tissue.

A need in the art therefore exists for a surgical fastening apparatus having a knife which minimizes the wisping of tissue during the severing operation. There is also a need in the art for surgical fastening apparatus capable of severing selected tough or resilient body tissue. Such surgical fastening apparatus would facilitate the severing of body tissue in adjoining operations via either open surgical procedures or endoscopic and laparascopic procedures by providing means for completely severing selected body tissue in a single actuation of instrumentation, thereby eliminating a need for subsequent introduction of instrumentation into the body.

SUMMARY OF THE INVENTION

The present invention improves upon prior art surgical fastening instruments by providing a knife with a non-linear cutting edge which successfully severs tissue while effectively eliminating the wisping of tissue. The intermediate portion of the cutting edge, disposed between a first upper and second lower portion of the cutting edge, is formed with at least one of said first upper and second lower portions distal to it. The non-linear cutting edge with distal first upper portion and/or second lower portion of the present invention allows the surgeon to reliably and fully sever the selected body tissue thereby eliminating the need for a subsequent procedure to sever remaining wisped tissue.

BRIEF DESCRIPTION OF THE DRAWINGS

FIG. 1 is perspective view of a knife having a nonlinear cutting blade in accordance with one embodiment of the present invention.

FIG. 2 is a side-view of the knife of FIG. 1.

FIG. 3 is a front view of the cutting edge of the instrument of FIG. 1.

FIG. 4 is a sectional view taken along line 4—4 of FIG. 3.

FIG. 5 is a perspective view of a fastener cartridge incorporating the knife of FIG. 1 therein.

FIG. 6 is a side view of another preferred embodiment of a nonlinear cutting blade in accordance with the present invention.

FIG. 6a is an enlarged view of the nonlinear cutting blade of FIG. 6.

FIG. 7 is a side view of another preferred embodiment of a nonlinear cutting blade in accordance with the present invention.

FIG. 8 is a side view of another preferred embodiment of a nonlinear cutting blade in accordance with the present invention.

FIG. 9 is a side view of another preferred embodiment of a nonlinear cutting blade in accordance with the present invention.

FIG. 9a is an enlarged view of the nonlinear cutting blade of FIG. 9.

DETAILED DESCRIPTION OF THE PREFERRED EMBODIMENTS

Figure 12:
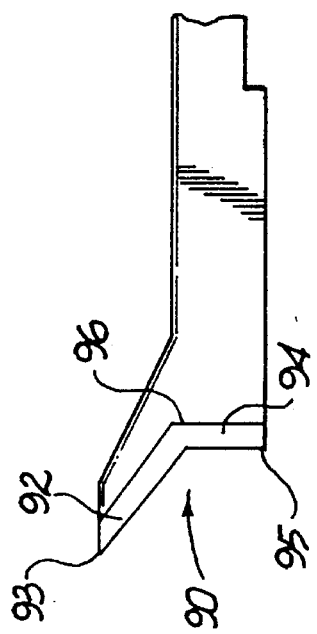
FIG. 12 is a side view of another preferred embodiment of a nonlinear cutting blade in accordance with the present invention.

As can be seen in FIGS. 1 and 2, surgical knife 10 of the present invention includes a knife body 12 tissue engaging portion 14 having a nonlinear cutting edge 16 and an attachment portion 18. In describing the knife of the present invention, the term "distal" refers to a direction of the knife away from the user and towards the patient's body tissue while the term "proximal" refers to a direction towards the user and away from the patient's body tissue.

Figure 16:
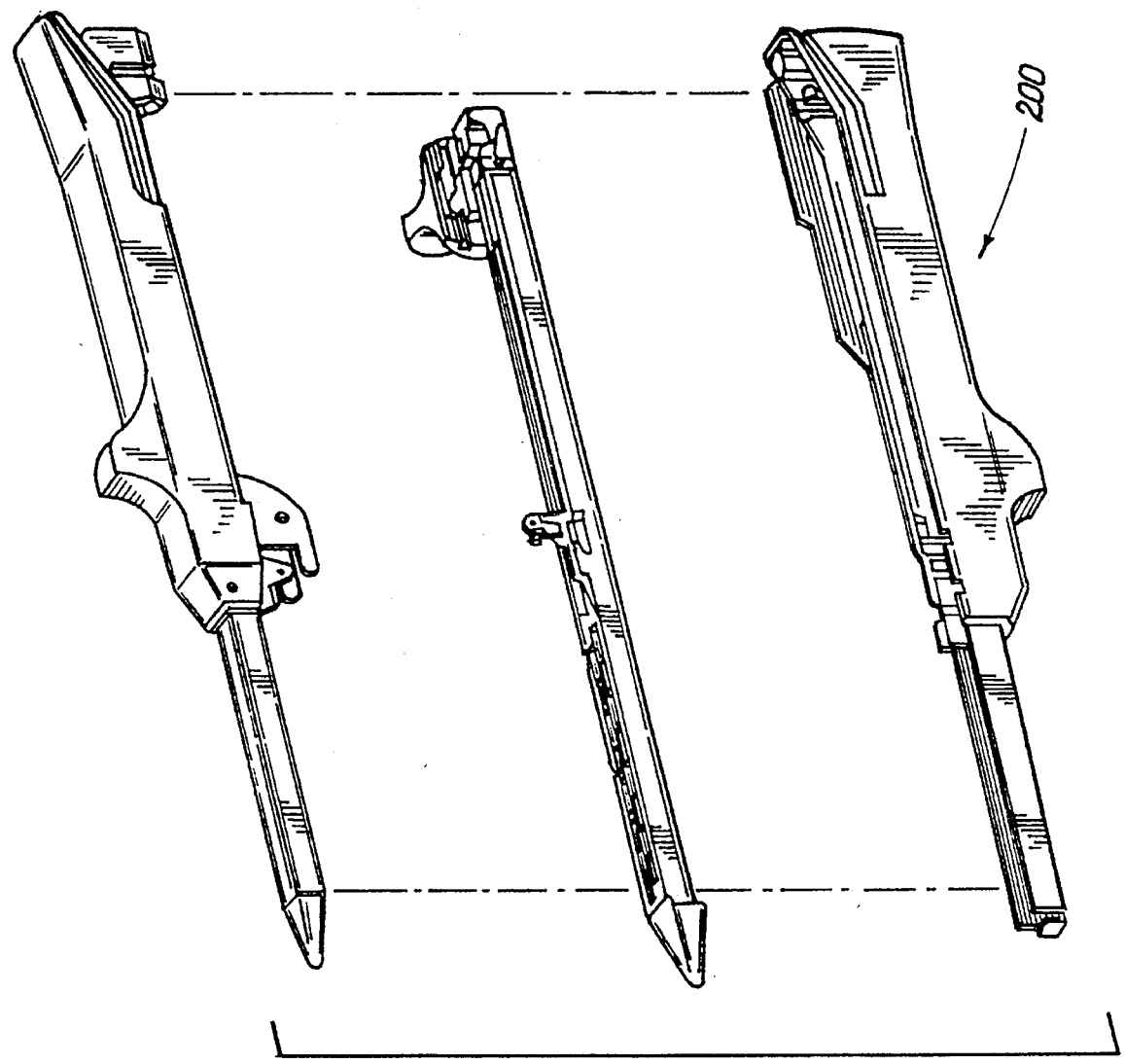
FIGS. 16 and 16a show surgical instruments of the type with which the cutting blade of the present invention may be employed.
Figure 16A:
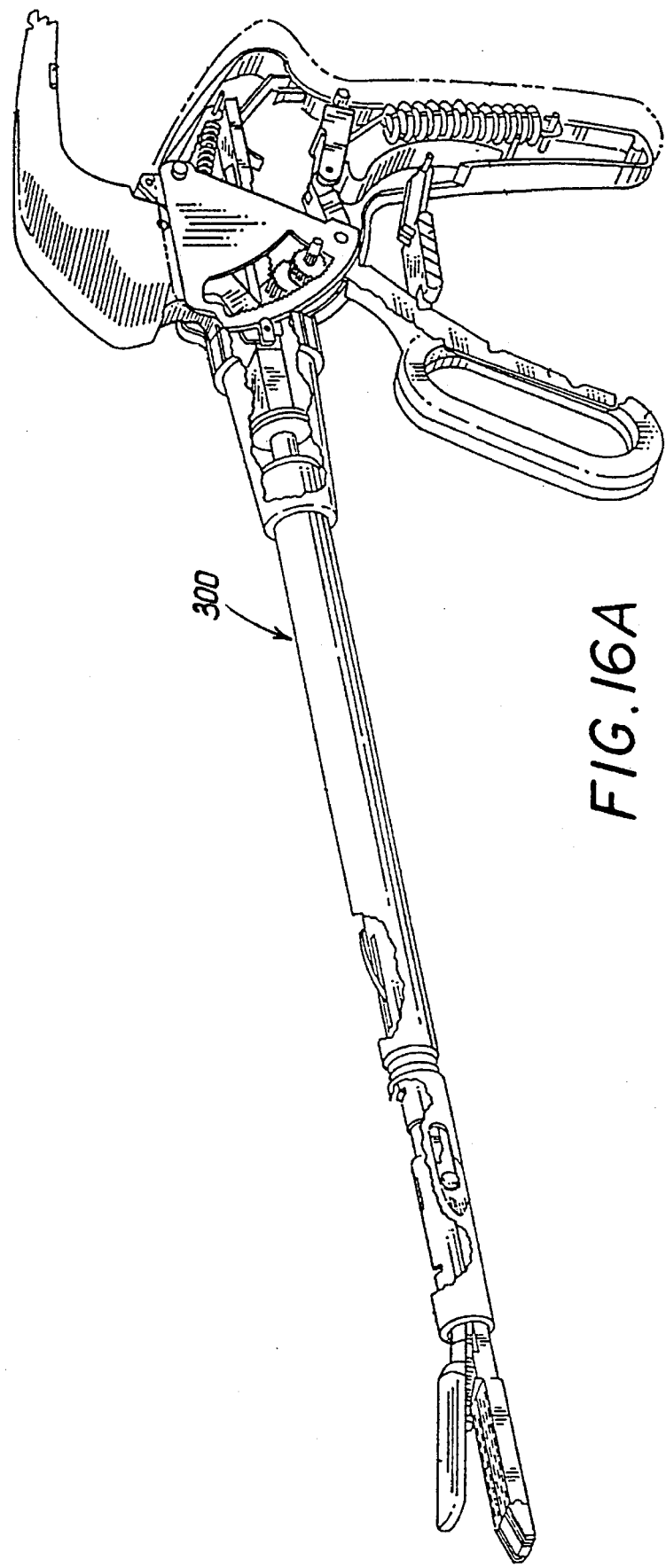

As noted above, instruments capable of both the severing and adjoining of tissue are known in the art. Several patents which disclose such instruments have been incorporated herein by reference. The cutting means of the present invention is adapted and intended to be used with any such instrument. FIGS. 16a and 16b show two instruments 200, 300 with which the cutting means of the present invention may be employed. These two instruments are merely illustrative and are to be construed as limiting the apparatus with which the present invention may be efficaciously employed.

As can be seen in FIGS. 3 and 4, the nonlinear cutting edge 16 is defined by the intersection of tapered lateral edges 20 of tissue engaging portion 14. The nonlinear cutting edge 16 of FIGS. 1–4 provides more effective severing means for the surgeon. As the selected body tissue is severed by the nonlinear cutting edge 16, the nonlinear nature and resulting geometry of cutting edge 16 helps to prevent the tissue from "riding up" the cutting edge 16 and into contact with the upper finger of the apparatus.

FIG. 5 is illustrative of a typical fastener cartridge assembly of a surgical fastening instrument. Fastener cartridge 22 includes an elongated support channel 28 having vertical wall members 23L and 23R longitudinally extending proximally from distal end 24 of the cartridge 22. Staple holding portions 26L and 26R of cartridge 22 have a longitudinally extending slot 25 for receiving the knife 10 and staple slots 27 for holding staples to be driven through tissue. Knife 10 is distally moved along slot 25, between staple holding portions 26L and 26R and through stapled tissue by actuation of means connected to the attachment portion 18 of knife 10. In describing the cutting edge 16 of knife 10, the term "upper" refers to a portion of the cutting edge 16 most removed from slot 25 while the term "lower" refers to a portion of the cutting edge 16 adjacent to slot 25.

In a preferred embodiment of the present invention, as shown in FIGS. 6 and 6a cutting edge 30 has a first upper portion 32, a second lower portion 34, an intermediate portion 36 lying at the intersection of the first upper portion 32 and second lower portion 34. As seen in FIG. 6a, the first upper portion 32 and second lower portion 34 of the instrument of FIG. 6 form an angle $\phi$ equal to 90°. Other values for $\phi$ are equally useful and include values wherein $0 < \phi < 180°$.

Another aspect of the present invention is a multiple member design of the cutting edge. An example of such a multiple member design is shown in FIGS. 6 and 6a where a two member design is used to form cutting edge Nonlinear cutting edge 30 is formed by the union of a first upper member 38 and a second lower member 39. The two member design provides means for achieving desired geometry of the nonlinear cutting edge 30 while minimizing the costs associated with machining a single piece of raw material to obtain said geometry.

As the cutting edge 30 is moved into contact with the tissue, second lower portion 34 provides the initial severing of tissue. As the cutting edge continues to move in a tissue engaging direction, tissue is continually severed by the second lower portion 34 and then by the intermediate portion 36. At this time, some tough tissue may have ridden up the second lower portion 34 and thereby be partially severed or unsevered. As the cutting edge 30 is further moved in a tissue engaging direction, the partially severed and unsevered tissue comes into contact with the first upper portion 32 of cutting edge 30. The first upper portion 32, lying distal to the intermediate portion 36, provides an advantageous geometry for completely severing the tissue "riding up" from the intermediate portion 36 and thereby preventing the wisping of tissue over said first upper portion 32.

Another embodiment of a nonlinear cutting edge according to the present invention is shown in FIG. 7. A cutting edge 40 has an intermediate portion 42 disposed between a first upper curvilinear portion 44 and a second lower curvilinear portion 46, the intermediate portion 42 forming a substantially sinusoidal shape having a plurality of radii of curvature.

Another embodiment of a nonlinear cutting edge according to the present invention is shown in FIG. 8. A cutting edge 50 has a first upper portion 52 terminating at upper distal tip 53, a second lower portion 54 terminating at a lower distal tip 55, the nonlinear cutting edge 50 has an intermediate portion 56 at the intersection of the first upper portion 52 and second lower portion 54. The upper distal tip 53 lying distal to the intermediate portion 56 and proximal with respect to the lower distal tip 55.

Another embodiment of a nonlinear cutting edge according to the present invention is shown in FIGS. 9 and 9a. A nonlinear cutting edge 60 has a first upper portion 62 terminating at an upper distal tip 63, a second lower portion 64 terminating at a lower distal tip 65, the nonlinear cutting edge 60 having an intermediate portion 66 at the intersection of the first upper portion 62 and second lower portion 64. The lower distal tip 65 lying distal to the intermediate portion 66 and proximal with respect to the upper distal tip 63. As seen in FIG. 9a, a first plane 62p is defined by first upper, portion 62 and a second plane 64p is defined by second lower portion 64 of the instrument of FIG. 6. The first plane 62p and second plane 64p, respectively shown in phantom, form an angle φ wherein 60°<φ<120°.

Tissue, when engaged by nonlinear cutting edge 60, is first put into contact with second lower portion 64. Tough tissue "riding up" second lower portion 64 is directed towards intermediate portion 66. As the cutting edge 60 continues to move in a tissue engaging direction, the tough tissue which is either partially severed or unsevered is further directed up against first upper portion 62 for complete severing. The geometry created by having upper distal tip 63 distal to intermediate portion 66 once again facilitates complete severing and thereby prevents the wisping of tissue over first upper portion 63.

Figure 10:
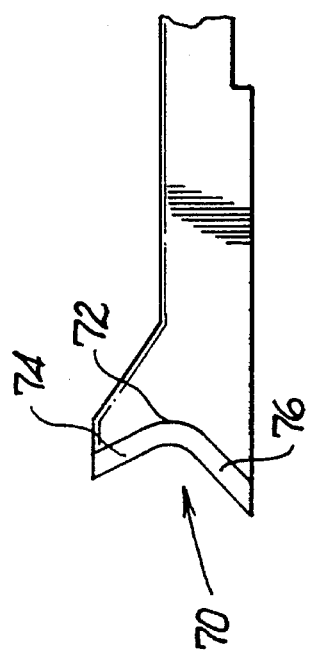
FIG. 10 is a side view of another preferred embodiment of a nonlinear cutting blade in accordance with the present invention.

Another embodiment of a nonlinear cutting edge according to the present invention is shown in FIG. 10. Cutting edge 70 has an intermediate portion 72 disposed between a first upper portion 74 and second lower portion 76. The intermediate portion 72 forming a substantially concave shape having a plurality of radii of curvature.

Figure 11:
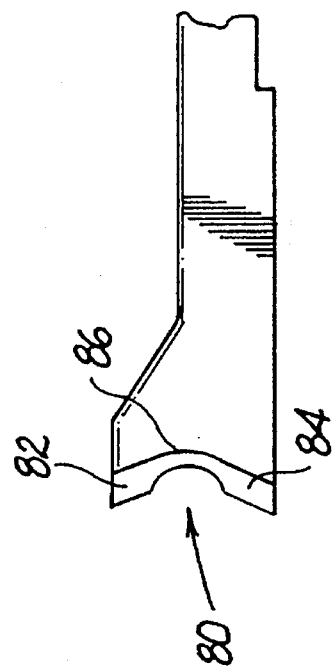
FIG. 11 is a side view of another preferred embodiment of a nonlinear cutting blade in accordance with the present invention.

Another embodiment of the nonlinear cutting edge according to the present invention is shown in FIG. 11. A cutting edge 80 has a first upper portion 82, a second lower portion 84 and an intermediate portion 86 disposed between the first upper portion 82 and second lower portion 84. Intermediate portion 86 forms a substantially concave shape having a plurality of radii of curvature.

Another embodiment of a nonlinear cutting edge according to the present invention is shown in FIG. 12. A cutting edge 90 has a first upper portion 92 terminating at an upper distal tip 93, a second lower portion 94 terminating at a lower distal tip 95, the nonlinear cutting edge 90 having an intermediate portion 96 at the intersection of the first upper portion 92 and second lower portion 94. The upper distal tip 93 lying distal to intermediate portion 96 in comparison to lower distal tip 95.

Figure 13:
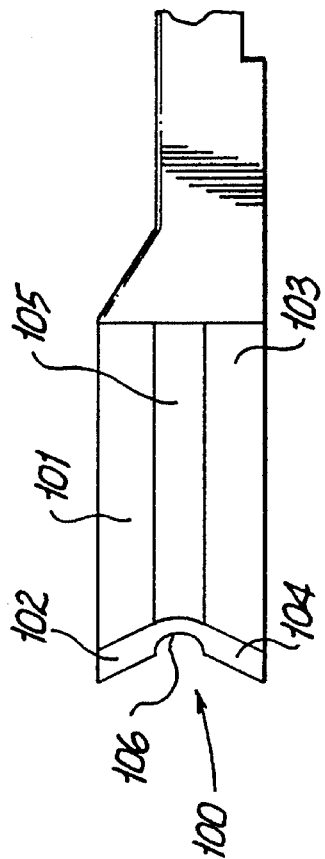
FIG. 13 is a side view of another preferred embodiment of a nonlinear cutting blade in accordance with the present invention.

FIG. 13 illustrates another embodiment of a nonlinear cutting edge according to the present invention. A cutting edge 100 is formed by the union of a first portion 102 of a first member 101, a second portion 104 of a second member 103, and an intermediate portion 106 of a third member 105.

Figure 14:
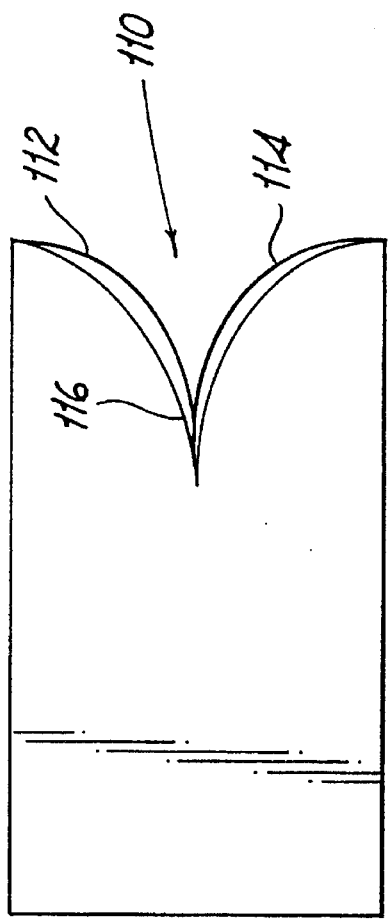
FIG. 14 is a side view of another preferred embodiment of a nonlinear cutting blade in accordance with the present invention.
Figure 15:
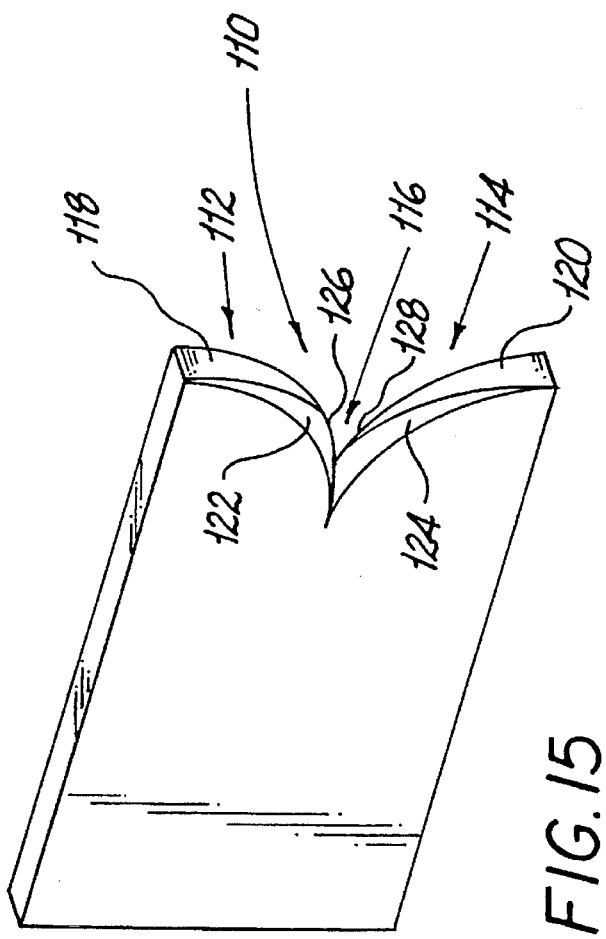
FIG. 15 is a perspective view of the nonlinear cutting blade of FIG. 14.

Another embodiment of a nonlinear cutting edge according to the present invention is shown in FIGS. 14 and 15. Cutting edge 110 has a first upper portion 112, a second lower portion 114 and a generally V-shaped intermediate portion 116 disposed between upper portion 112 and lower portion 114. Both upper portion 112 and lower portion 114 are shaped as cubic parabolas, i.e., a three dimensional object having a parabolic cross section wherein both noncutting surfaces 118 and 120 gradually give way to cutting surfaces 122 and 124, respectively. Cutting surfaces symmetrical to cutting surfaces 122 and 124 (not shown) converge to and join cutting surfaces 122 and 124 at V-shaped portion 116 to form cutting edges 126 and 128, respectively. In operation, the cubic parabola configuration provides for minimal tissue acceleration and a smooth change of direction.

Inasmuch as the present invention is subject to many variations, modifications and changes in detail, the subject matter discussed above and shown in the accompanying drawings is intended to be illustrative only and not to be taken in a limiting sense.

What is claimed is:

1. In a surgical fastening instrument having a plurality of fasteners and a knife for severing tissue, the improvement comprising:

a nonlinear cutting edge formed on a tissue engaging portion of said knife, the cutting edge having a first convex curved portion, a second convex curved portion, and an intermediate concave curved portion disposed between said first and second portions, wherein the cutting edge forms a substantially sinusoidal shape having a plurality of radii of curvature.

2. The surgical fastening instrument of claim 1 wherein a first plane defined by said first portion and a second plane defined by said second portion are disposed at an angle of between 0° and 180° with respect to one another.

3. The surgical fastening instrument of claim 2 wherein said first and second planes are disposed at an angle of between 60° and 120° with respect to one another.

4. The surgical fastening instrument of claim 1 wherein said first portion is distal to said second portion.

5. The surgical fastening instrument of claim 1 wherein said second portion is distal to said first portion.

6. The surgical fastening instrument of claim 1 wherein said first portion and said second portion are both distal to said intermediate portion.

7. In a surgical fastening instrument having a plurality of fasteners and a knife for severing tissue, the improvement comprising:

a cutting edge constructed from at least two members, said members having respective cutting portions, said members joined so that said cutting portions form a nonlinear cutting edge on a tissue engaging portion of said knife.

8. The surgical fastening instrument of claim 7 wherein each of said cutting portions is linear.

9. The surgical instrument of claim 7 wherein said nonlinear cutting edge is formed by the union of two of said members.

10. The surgical fastening instrument of claim 7 wherein each of said cutting portions are curvilinear.

11. The surgical fastening instrument of claim 7 wherein said nonlinear cutting edge forms a substantially concave curvilinear shape.

12. The surgical fastening instrument of claim 7 wherein said nonlinear cutting edge is formed by the union of a first member, a second member, and a third member, said first member forming said first portion, said second member forming said second portion, and said third member forming said intermediate portion.

13. The surgical fastening instrument of claim 12 wherein said first member and said second member are linear.

14. In a surgical fastening instrument having a plurality of fasteners and a knife for severing tissue, the improvement comprising:

a tissue engaging surface disposed on a distal end of said knife, the tissue engaging surface having a first portion, a second portion, and an intermediate portion disposed therebetween, at least one said first and second portions having at least one non-cutting surface sloping proximally and inwardly toward said intermediate portion and converging with at least one cutting surface, the at least one cutting surface being at least partially disposed between the at least one non-cutting surface and the intermediate portion and sloping proximally and inwardly from a proximal portion of said non-cutting surface toward said intermediate portion.

15. The surgical fastening instrument of claim 14 wherein two inwardly sloping cutting surfaces converge to form an inwardly sloping cutting edge.

16. The surgical fastening instrument of claim 15 wherein the two inwardly sloping cutting surfaces are symmetrical in configuration.

17. The surgical fastening instrument of claim 14 wherein at least a portion of said knife forms at least a portion of a cubic parabola.

18. The surgical fastening instrument of claim 14 wherein a portion of the inwardly sloping non-cutting surface narrows in width as it converges with the inwardly sloping cutting surface.

* * * * *